United States Patent [19]

Glamkowski

[11] Patent Number: 4,914,102

[45] Date of Patent: Apr. 3, 1990

[54] N-AMINOCARBAMATES RELATED TO PHYSOSTIGMINE, PHARMACENTICAL COMPOSITIONS AND USE

[75] Inventor: Edward J. Glamkowski, Warren, N.J.

[73] Assignee: Hoechst Roussel Pharmaceuticals, Inc., Somerville, N.J.

[21] Appl. No.: 413,901

[22] Filed: Sep. 28, 1989

[51] Int. Cl.[4] .................. A61K 31/40; A61K 31/535; C07D 487/04

[52] U.S. Cl. ................. 514/232.8; 514/253; 514/322; 514/411; 544/142; 544/372; 546/199; 548/429

[58] Field of Search ............... 544/142, 372; 546/199; 548/429; 514/232.8, 285, 322, 411

[56] References Cited

U.S. PATENT DOCUMENTS 4,791,107 12/1988 Hammer et al. .................... 548/429

4,831,155 5/1989 Brufani et al. ....................... 548/429

Primary Examiner—Robert W. Ramsuer
Attorney, Agent, or Firm—Tatsuya Ikeda

[57] ABSTRACT

There are disclosed various derivatives of physostigmine and related compounds of the formula below,

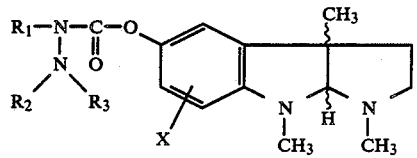

where $X, R_1, R_2$ and $R_3$ are as defined in the specification, which compounds are useful for alleviating various memory dysfunctions characterized by a cholinergic deficit such as Alzheimer's disease.

23 Claims, No Drawings

N-AMINOCARBAMATES RELATED TO PHYSOSTIGMINE, PHARMACENTICAL COMPOSITIONS AND USE

The present invention relates to compounds of the formula,

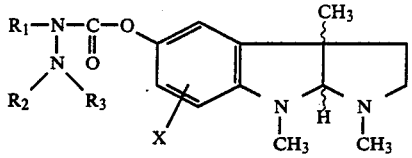

where X is hydrogen, halogen or loweralkyl; and $R_1$, $R_2$ and $R_3$ are each independently hydrogen, loweralkyl, cycloalkyl, arylloweralkyl or aryl, or alternatively the group—$NR_2R_3$ taken as a whole constitutes

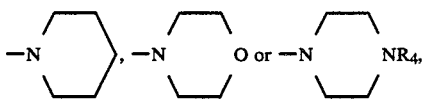

$R_4$ being hydrogen or loweralkyl, and stereo, optical and geometric isomers thereof, as well as racemic mixtures thereof, which compounds are useful for alleviating various memory dysfunctions characterized by a cholinergic deficit such as Alzheimer's disease.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term cycloalkyl shall mean a cycloalkyl group having from 3 to 7 carbon atoms in the ring. Said cycloalkyl group may be substituted with 1 or 2 loweralkyl groups.

The term halogen shall mean fluorine, chlorine, bromine or iodine.

The term aryl shall mean an unsubstituted phenyl group or a phenyl group substituted with 1, 2 or 3 substituent groups each of which being independently loweralkyl, halogen, nitro, loweralkoxy, hydroxy or trifluoromethyl.

In structural formulas depicting the compounds of this invention, heavy lines ( ▬ ) coming out of the 3a-carbon and 8a-carbon of the 1,2,3,3a,8,8a-hexahydropyrrolo[2,3-b]indole ring system signify that the two substituents are above the average plane of the three-ring system, whereas dotted lines ( ∙∙∙∙∙ ) signify that the two substituents are below the average plane of the three-ring system, and wavy lines (〜〜〜) signify that the two substituents are both either above or below said average plane. Because of conformational constraints, the two substituents at the 3a- and 8a-positions must be both above said average plane or both below said average plane. Thus, in formula (I), the substituents at the 3a- and 8a-carbons are cis inasmuch as they are on the same side of the three ring system. Where said substituents are both above the average plane of the three ring system, the configuration will be referred to as 3aS-cis and where both substituents are below the average plane of the ring, the configuration will be referred to as 3aR-cis. These two types of configuration are depicted below.

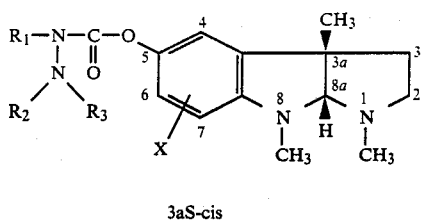

3aS-cis

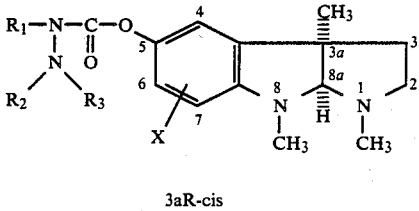

3aR-cis

Throughout the specification and the appended claims, where the inventor intends to designate in a single formula (to save space) that the compound is 3aS-cis, or 3aR-cis, or a racemic or other mixture of the two, that formula will contain wavy lines, as depicted below.

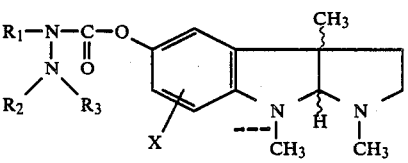

It is the intent of the present inventor to claim both of said cis isomers, namely, 3aS-cis isomer and 3aR-cis isomer for each compound name or structural formula although sometimes only one isomer is shown in the specification in order to save space. It is also the intent of the present inventor to claim all mixtures of the 3aS-cis and 3aR-cis isomers including the racemic mixture (1:1 ratio of 3aS-cis:3aR-cis).

The compounds of the present invention can be prepared by utilizing the synthetic scheme described below, where the notations X, $R_1$, $R_2$ and $R_3$ have the respective meanings as defined above.

SYNTHETIC SCHEME

Eseroline (or a substituted eseroline) depicted by Formula II is allowed to react with 1,1'-carbonyldiimidazole and thereafter a compound of the formula

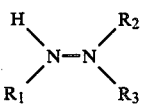

is added to the reaction mixture to obtain Compound I.

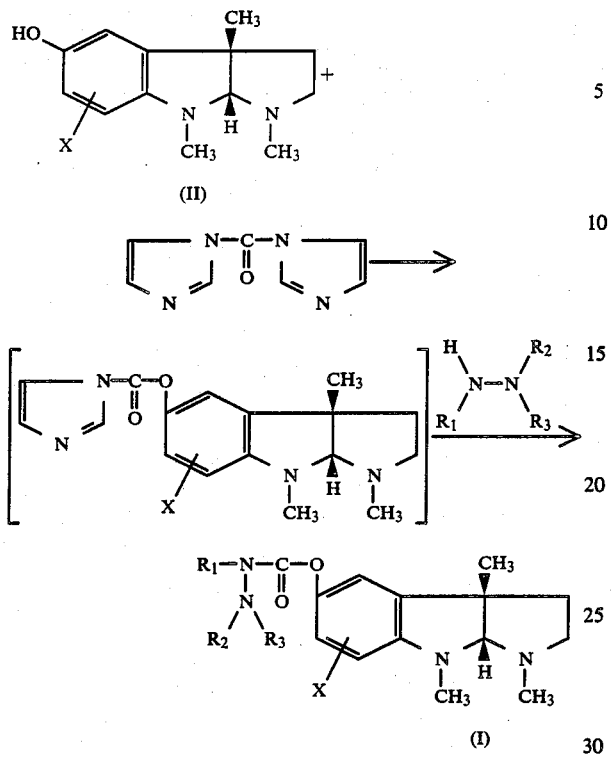

Said reaction between compound II and 1,1'-carbonyldiimidazole is typically conducted by preparing a degassed solution of compound II in a suitable solvent such as anhydrous tetrahydrofuran, adding 1,1'-carbonyldiimidazole to the solution and stirring the solution at room temperature for a suitable length of time such as one hour. The carbamation reaction is typically conducted by adding the hydrazine compound to the solution obtained above and stirring the solution at room temperature for a few hours.

The compounds of formula I of the present invention are useful in the treatment of various memory dysfunctions characterized by decreased cholinergic function, such as Alzheimer's disease.

This utility is manifested by the ability of these compounds to inhibit the enzyme acetylcholinesterase and thereby increase acetylcholine levels in the brain.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer patients. Therefore, specific inhibitors of brain AChE (as opposed to serum AChE) will give rise to fewer side effects and thus lower toxicity than physostigimine (an unspecific AChE inhibitor). The in vitro inhibition of acetylcholinesterase activity in rat striatum was determined according to the method described below. Results of some of the compounds of this invention as well as that of physostigmine are presented in Table 1.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinominetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying cholinesterase activity. This is a modification of the method of Ellman et al., Biochem. Pharmacol. 7, 98 (1961).

Procedure

A. Reagents
  1. 0.05 M Phosphate buffer, pH 7.2
     (a) 6.85 g $NaH_2PO_4.H_2O$/100 ml distilled $H_2O$
     (b) 13.40 g $Na_2HPO_4.7H_2O$/100 ml distilled $H_2O$
     (c) add (a) to (b) until pH reaches 7.2
     (d) Dilute 1:10
  2. Chromogen-substrate buffer
     (a) 9.9 mg 5,5-dithiobisnitrobenzoic acid (DTNB) (0.25 mM)
     (b) 99 mg s-acetylthiocholine chloride (5 mM)
     (c) q.s. to 100 ml with 0.05 M phosphate buffer, pH 7.2 (reagent 1)
  3. For most assays, a 2 mM stock soluion of the test drug is made up in a suitable solvent and serially diluted such that the final concentration in the preincubation step ranges from $10^{-3}$ to $10^{-6}$ M. Different concentrations may be used depending on the potency of the drug.

B. Tissue Preparation
  Male Wistar rats are decapitated, brains rapidly removed, corpora striata dissected free, weighed and homogenized in 19 volumes (approximately 7 mg protein/ml) of 0.05 M phosphate buffer, pH 7.2 using a Potter-Elvehjem homogenizer. A 50 microliter aliquot of the homogenate is added to 50 microliter vehicle of various concentrations of the test drug and preincubated for 10 minutes at room temperature.

C. Assay
  1. For routine $IC_{50}$ determinations the Abbott Bichromatic Analyzer, ABA-100, is used to determine acetylcholinesterase activity.
     Instrument settings
       Filter: 450–415
       Incubation temperature: 30° C.
       Decimal point: 0000.
       Analysis time: 5 minutes
       Carousel Revolution: 3
       Reaction direction:
         down
         endpoint
       Syringe plate: 1:101 dilution
       Following the 10 minute preincubation of the tissue (enzyme) with the inhibitor, the samples are mixed with the substrate chromogen buffer by the ABA-100. Using the indicated instrument settings the ABA-100 automatically reads the color reaction and prints out the results in enzyme units after 15 minutes.
2. The enzyme activity can also be measured with Gilford 250 spectrophotometer. This method is used for more accurate kinetic measurements.
Instrument settings
  Lamp: visible
  Filter: no filter
  Wavelength: 412 nm
  Slit width: 0.2 mm
  Selection: small aperture
  Calibrated absorbance: 1.0 unit full scale
  Chart speed: 0.5 cm/min Reagents are added to the reference and sample side of a split curvette as follows:

| Reference | Sample |
| --- | --- |
| 0.8 ml 0.05 M phosphate buffer | 0.8 ml 0.05 M phosphate buffer |
| 0.8 ml Chromogen-substrate buffer | 0.8 ml Chromogen-substrate buffer |
| | 10 microliter enzyme (tissue homogenate) |

The uninhibited activity of the enzyme (tissue homogenate) is first determined. Test drugs are made up in a suitable solvent and added in suitable dilutions to the buffer vehicle. The reaction rate is determined by the slope of the recorded absorbance change. The actual rate (moles/liter/min) can be calculated as described in the following formula:

$$\text{rate (moles/liter/min)} = \text{slope}/(1.36 \times 10^4)$$

TABLE 1

| Compound | Inhibitory Concentration ($10^{-6}$ M) Brain AChE |
| --- | --- |
| (3aS-cis)-1,2,3,3a,8,8a-hexahydro-1,3a,8-trimethyl-pyrrolo[2,3-b]indol-5-yl piperidinylcarbamate | 0.59 |
| (3aS-cis)-1,2,3,3a,8,8a-hexahydro-1,3a,8-trimethyl-pyrrolo[2,3-b]indol-5-yl 4-morpholinylcarbamate (Reference Compound) | 1.60 |
| Physostigmine, namely, (3aS-cis)-1,2,3,3a,8,8a-hexahydro-1,3a,8-trimethyl-pyrrolo[2,3-b]indol-5-ol methylcarbamate | 0.10 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of the invention include those listed below as well as the 3aR-cis isomers thereof and mixtures of the 3aS-cis and 3aR-cis isomers including the racemix mixtures:

(3aS-cis)-1,2,3,3a,8,8a-hexahydro-1,3a,8-trimethylpyrrolo[2,3-b]indol-5-yl 4-morpholinyl carbamate;

(3aS-cis)-1,2,3,3a,8,8a-hexahydro-1,3a,8-trimethylpyrrolo[2,3-b]indol-5-yl 1-piperidinylcarbamate;
(3aS-cis)-1,2,3,3a,8,8a-hexahydro-1,3a,8-trimethylpyrrolo[2,3-b]indol-5-yl 2-benzylhydrazinecarboxylate;
(3aS-cis)-1,2,3,3a,8,8a-hexahydro-1,3a,8-trimethylpyrrolo[2,3-b]indol-5-yl 2-(2-phenylethyl)hydrazinecarboxylate;
[3aS-[3aα,5(R*), 8aα]]-1,2,3,3a,8,8a-hexahydro-1,3a,8-trimethylpyrrolo[2,3-b]indol-5-yl 2-(1-phenylethyl)hydrazinecarboxylate;
[3aS-[3aα,5(S*), 8aα]]-1,2,3,3a,8,8a-hexahydro-1,3a,8-trimethylpyrrolo[2,3-b]indol-5-yl 2-(1-phenylethyl)hydrazinecarboxylate;
(3aS-cis)-1,2,3,3a,8,8a hexahydro-1,3a,8 -trimethylpyrrolo[2,3-b]indol-5-yl 2-heptylhydrazinecarboxylate;
(3aR-cis)-1,2,3,3a,8,8a-hexahydro-1,3a,8 -trimethylpyrrolo[2,3-b]indol-5-yl 1-piperidinylcarbamate;
cis-(±)-1,2,3,3a,8,8a-hexahydro-1,3a,8-trimethylpyrrolo[2,3-b]indol-5-yl 1-piperidinylcarbamate;
(3aS-cis)-7-bromo-1,2,3,3a,8,8a-hexahydro-1,3a,8-trimethylpyrrolo[2,3-b]indol-5-yl 1-piperidinylcarbamate;
(3aS-cis)-7-bromo-1,2,3,3a,8,8a-hexahydro-1,3a,8-trimethylpyrrolo[2,3-b]indol-5-yl 4-morpholinylcarbamate;
(3aS-cis)-1,2,3,3a,8,8a-hexahydro-1,3a,8-trimethylpyrrolo[2,3-b]indol-5-yl 2,2dimethylhydrazinecarboxylate;
(3aS-cis)-1,2,3,3a,8,8a-hexahydro-1,3a,8-trimethylpyrrolo[2,3-b]indol-5-yl 1,2-dimethylhydrazinecarboxylate;
(3aS-cis)-1,2,3,3a,8,8a-hexahydro-1,3a,8-trimethylpyrrolo[2,3-b]indol-5-yl 2-cyclohexylhydrazinecarboxylate;
(3aS-cis)-1,2,3,3a,8,8a-hexahydro-1,3a,8-trimethylpyrrolo[2,3-b]indol-5-yl 2-phenylhydrazinecarboxylate;
(3aS-cis)-1,2,3,3a8,8a-hexahydro-1,3a,8-trimethylpyrrolo[2,3-b]indol-5-yl 2-(3chlorophenyl)hydrazinecarboxylate; and
(3aS-cis)-1,2,3,3a,8,8a-hexahydro-1,3a,7,8-tetramethylpyrrolo[2,3-b]indol-5-yl 1-piperidinylcarbamate.

The following examples are presented in order to illustrate this invention.

EXAMPLE 1

(3aS-cis)-1,2,3,3a,8,8a-hexahydro-1,3a,8-trimethylpyrrolo[2,3-b]indol-5-yl 4-morpholinylcarbamate Eseroline (3 g) and 1,1'-carbonyldiimidazole (2.3 g) were heated in 150 ml dry tetrahydrofuran (THF) at reflux under nitrogen for one hour. After cooling to +5° C., 0.5 g imidazole was added and a solution of 4-aminomorpholine (3 g) in 30 ml dry THF was dropped into the mixture within 30 minutes. When the addition was complete the mixture was warmed to room temperature and stirred for five hours and thereafter stored in a refrigerator overnight. The THF was evaporated and the oily residue purified by chromatography on neutral alumina with $CH_2Cl_2$/MeOH (95:5). The resulting oil was crystallized from ether/hexane to give a solid (0.6 g) which was combined with 0.5 g obtained from similar experiments and recrystallized from the same solvent mixture. This yielded 1.0 g of crystals, m.p. 115°–117° C.

ANALYSIS:
Calculated for $C_{18}H_{26}N_4O_3$: 62.41%C, 7.56H, 16.17%N.
Found: 62.27%C, 7.65%H, 16.35%N.

EXAMPLE 2

(3aS-cis)-1,2,3,3a,8,8a-hexahydro-1,3a,8-trimethylpyrrolo[2,3-b]indol-5-yl 1-piperidinylcarbamate A degassed solution of eseroline (2 g) in 40 ml dry THF was treated with 1,1'-carbonyldiimidazole (1.7 g) and heated at reflux for one hour under nitrogen. After this, the solution was cooled by means of an ice/water mixture and a solution of 1-aminopiperidine (1 g) and a spatula-tip of imidazole in 40 ml of dry THF were dropped into the solution within 30 minutes. Three hours later, the solvent was evaporated to leave an oil, which was purified by column chromatography (neutral alumina, dichloromethane/ethyl acetate (1:1)) to give 1 g of oil which was crystallized from a mixture of either/petroleum ether to give 800 mg of crystals which were combined with another crop and recrystallized from ether/petroleum ether to give 1.1 g of crystals, m.p. 82°–85° C.

ANALYSIS:
Calculated for $C_{19}H_{28}N_4O_2$: 66.25%C, 8.19%H, 16.26%N.
Found: 66.09%C, 8.35%H, 15.96%N.

We claim:
1. A compound of the formula

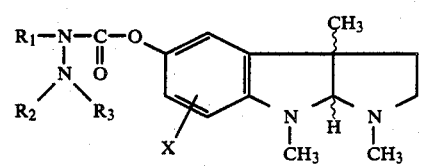

where X is hydrogen, halogen or loweralkyl; and $R_1$, $R_2$ and $R_3$ are each independently hydrogen, loweralkyl, cycloalkyl, arylloweralkyl or aryl, or alternatively the group —$NR_2R_3$ taken as a whole constitutes

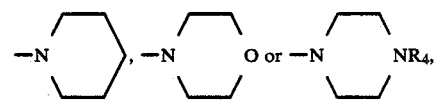

$R_4$ being hydrogen or loweralkyl; or a pharmaceutically acceptable acid addition salt thereof.

2. The compound as defined in claim 1, where X is hydrogen.
3. The compound as defined in claim 1, where X is halogen.
4. The compound as defined in claim 1, where X is loweralkyl.
5. The compound as defined in claim 1, which is (3aS-cis)-1,2,3,3a,8,8a-hexahydro-1,3a,8-trimethylpyrrolo[2,3-b]indol-5-yl 4-morpholinylcarbamate.
6. The compound as defined in claim 1, which is (3aS-cis)-1,2,3,3,a,8,8a-hexahydro-1,3a,8-trimethylpyrrolo[2,3-b]indol-5-yl 1 -piperidinylcarbamate.
7. The compound as defined in claim 1, which is (3aS-cis)-1,2,3,3a,8,8a-hexahydro-1,3a,8-trimethylpyrrolo[2,3-b]indol-5-yl 2-benzylhydrazinecarboxylate.
8. The compound as defined in claim 1, which is (3aS-cis)-1,2,3,3a,8,8a-hexahydro-1,3a,8-trimethylpyrrolo[2,3-b]indol-5yl 2-(2-phenylethyl)hydrazinecarboxylate.
9. The compound as defined in claim 1, which is [3aS-[3aα,5(R*), 8aα]]-1,2,3,3a,8,8a-hexahydro-1,3a,8- trimethylpyrrolo[2,3-b]-indol-5-yl 2-(1-phenylethyl)hydrazinecarboxylate.

10. The compound as defined in claim 1, which is [3aS-[3a α,5(S*), 8aα]]-1,2,3,3a,8,8a-hexahydro-1,3a,8-trimethylpyrrolo[2,3-b]indol-5-yl 2-(1-phenylethyl)hydrazinecarboxylate.

11. The compound as defined in claim 1, which is (3aS-cis)-1,2,3,3a,8,8a-hexahydro-1,3a,8-trimethylpyrrolo[2,3-b]indol-5-yl 2-heptylhydrazinecarboxylate.

12. The compound as defined in claim 1, which is (3aR-cis)-1,2,3,3a,8,8a-hexahydro-1,3a,8-trimethylpyrrolo[2,3-b]indol-5-yl 1-piperidinylcarbamate.

13. The compound as defined in claim 1, which is cis-(±)-1,2,3,3a, 8,8a-hexahydro-1,3a,8-trimethylpyrrolo[2,3-b]indol-5yl 1-piperidinylcarbamate.

14. The compound as defined in claim 1, which is (3aS-cis)-7-bromo-1,2,3,3a,8,8a-hexahydro-1,3a,8-trimethylpyrrolo-[2,3-b]indol-5-yl 1-piperidinylcarbamate.

15. The compound as defined in claim 1, which is (3aS-cis)-7-bromo-1,2,3,3a,8,8a-hexahydro-1,3a,8-trimethylpyrrolo[2,3-b]indol-5-yl 4-morpholinylcarbamate.

16. The compound as defined in claim 1, which is (3aS-cis)-1,2,3,3a,8,8a-hexahydro-1,3a,8-trimethylpyrrolo[2,3-b]indol-5-yl 2,2-dimethylhydrazinecarboxylate.

17. The compound as defined in claim 1, which is (3aS-cis)-1,2,3,3a,8,8a-hexahydro-1,3a,8-trimethylpyrrolo[2,3-b]indol-5yl 1,2-dimethylhydrazinecarboxylate.

18. The compound as defined in claim 1, which is (3aS-cis)-1,2,3,3a,8,8a-hexahydro-1,3a,8-trimethylpyrrolo[2,3-b]indol-5-yl 2-cyclohexylhydrazinecarboxylate.

19. The compound as defined in claim 1, which is (3aS-cis)-1,2,3,3a,8,8a-hexahydro-1,3a,8-trimethylpyrrolo[2,3-b]indol-5-yl 2-phenylhydrazinecarboxylate.

20. The compound as defined in claim 1, which is (3aS-cis)-1,2,3,3a,8,8a-hexahydro-1,3a,8-trimethylpyrrolo[2,3-b]indol-5-yl 2-(3-chlorophenyl)hydrazinecarboxylate.

21. The compound as defined in claim 1, which is (3aS-cis)-1,2,3,3a,8,8a-hexahydro-1,3a,7,8a-tetramethylpyrrolo[2,3-b]indol-5-yl 1-piperidinylcarbamate.

22. A pharmaceutial composition comprising a compound as defined in claim 1 in an amount effective for alleviating a memory dysfunction characterized by a cholinergic deficit and a suitable carrier therefor.

23. A method of treating a patient in need of relief from a memory dynsfunction characterized by a cholinergic deficit which comprises administering to such a patient an effective amount of a compound as defined in claim 1.

* * * * *